(12) United States Patent
Guger et al.

(10) Patent No.: US 9,662,031 B2
(45) Date of Patent: *May 30, 2017

(54) DEVICE FOR APPLYING ELECTRODE ASSEMBLIES

(71) Applicants: Christoph Guger, Pieberbach (AT); Guenter Edlinger, Graz (AT)

(72) Inventors: Christoph Guger, Pieberbach (AT); Guenter Edlinger, Graz (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/676,266

(22) Filed: Apr. 1, 2015

(65) Prior Publication Data
US 2016/0113542 A1 Apr. 28, 2016

Related U.S. Application Data

(63) Continuation of application No. 14/006,368, filed as application No. PCT/AT2012/000014 on Jan. 31, 2012, now Pat. No. 9,237,857.

(51) Int. Cl.
*A61B 5/0478* (2006.01)
*A61B 5/0408* (2006.01)
*A61B 5/00* (2006.01)

(52) U.S. Cl.
CPC ........ *A61B 5/04085* (2013.01); *A61B 5/0478* (2013.01); *A61B 5/6803* (2013.01); *A61B 5/6814* (2013.01); *A61B 2562/046* (2013.01)

(58) Field of Classification Search
CPC .............................. A61B 5/0478; A61B 5/6814
See application file for complete search history.

(56) References Cited

U.S. PATENT DOCUMENTS

| | | | | |
|---|---|---|---|---|
| 3,896,790 A | * | 7/1975 | Dikmen | A61B 5/0478 600/383 |
| 4,967,038 A | * | 10/1990 | Gevins | A61B 5/0017 600/383 |
| 8,620,401 B2 | * | 12/2013 | Yamashita | A61B 5/0478 600/383 |
| 9,237,857 B2 | * | 1/2016 | Guger | A61B 5/0478 |
| 2007/0238945 A1 | * | 10/2007 | Delic | A61B 5/0478 600/383 |
| 2010/0198042 A1 | * | 8/2010 | Popescu | A61B 5/6814 600/383 |
| 2011/0074396 A1 | * | 3/2011 | Liao | A61B 5/04085 324/121 R |
| 2012/0226127 A1 | * | 9/2012 | Asjes | A61B 5/04085 600/383 |

* cited by examiner

*Primary Examiner* — Lee S Cohen
(74) *Attorney, Agent, or Firm* — Dennemeyer & Associates, LLC

(57) ABSTRACT

The invention relates to a device comprising a number of electrode assemblies (10), which can be applied to the skin surface (4) of an animal or human being and by means of which voltages and currents can be tapped from the skin surface (4), and comprising a flexible, in particular extendable, retaining element (6) formed by a planar or film-like molded part. According to the invention, the electrode assemblies (10) comprise a main body (1) and a number of pin electrodes (2) that protrude from the main body (1) in the same direction, the electrode assemblies (10) are fastened to the retaining element (6), and the main body (1) of the respective electrode assembly (10) is connected to the retaining element (6), wherein the pin electrodes (2) of all electrode assemblies (10) protrude in the same direction.

17 Claims, 5 Drawing Sheets

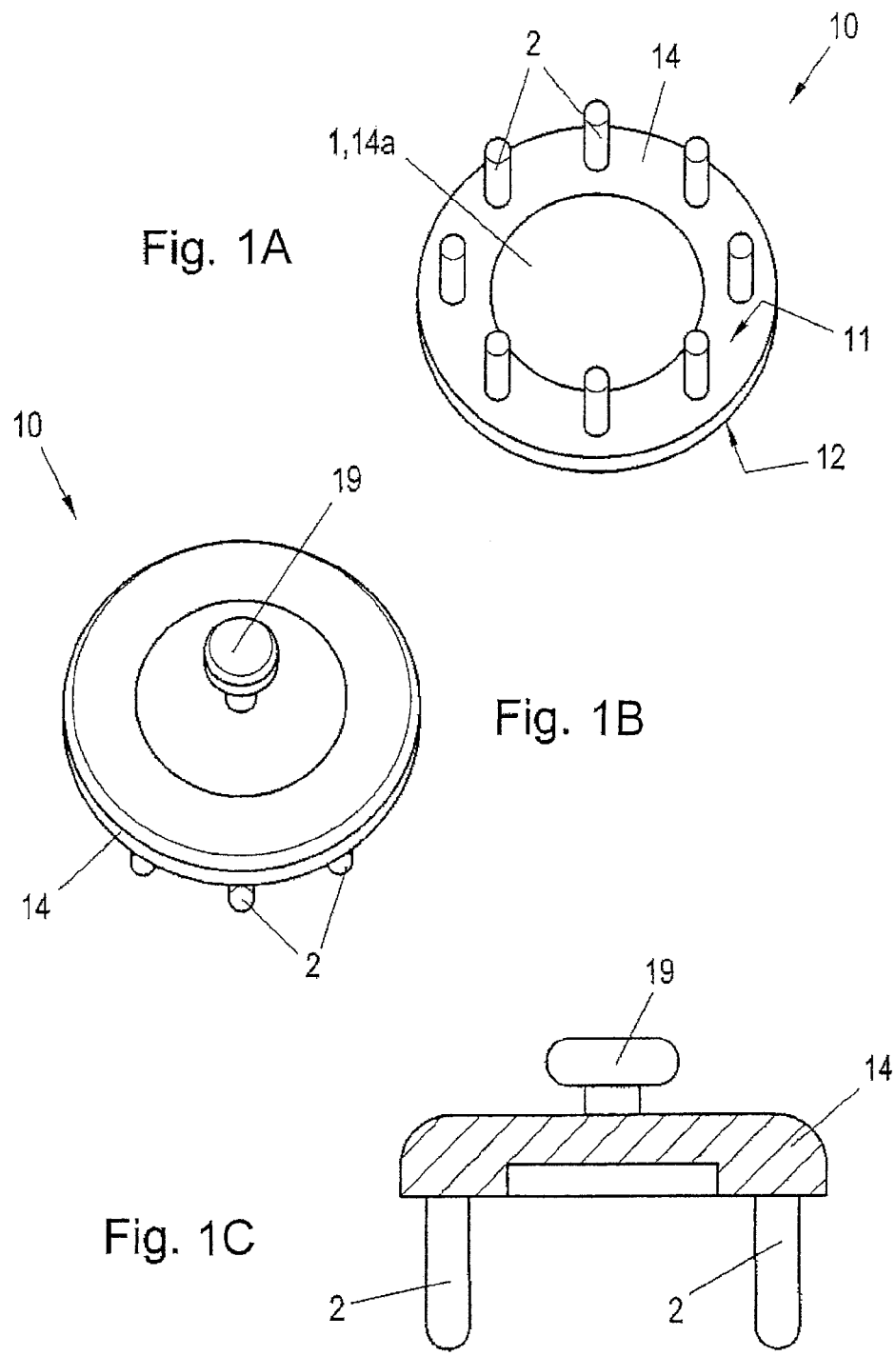

US 9,662,031 B2

DEVICE FOR APPLYING ELECTRODE ASSEMBLIES

CROSS-REFERENCE TO RELATED APPLICATIONS

The present invention is a continuation of U.S. patent application Ser. No. 14/006,368 filed Sep. 20, 2013, now U.S. Pat. No. 9,237,857, which in turn claims the priority of PCT/AT2012/000014 filed Jan. 31, 2012. These applications are incorporated by reference herein for all purposes.

BACKGROUND OF THE INVENTION

The invention relates to a device for applying electrode assemblies to the surface of the skin of an animal or human being, according to the independent claim 1.

SUMMARY OF THE INVENTION

In the following the animal or human at whose skin voltages or voltage differences are to be determined will be referred to as the "patient".

The inventive electrode assemblies are used in particular in the medical field for measuring brain currents or cardiac activity.

In the use of dry electrodes for detecting electrical signals in the interior of the body of the patient, correct positioning of the electrodes is an essential requirement. According to the state of the art, so-called spiders are used which fix the individual electrodes or electrode assemblies to the body part of the patient on which measurements are to be made, to provide maximal holding and problem-free contact of the electrodes.

Spiders have a plurality of arms on the ends of which individual electrodes are arranged. A problem with this is that the positions and orientation of the individual electrodes have to be adjusted to the particular form of the patient, and therefore numerous different adjustment steps have to be carried out in order to adapt the electrodes to the patient. A further problem is that the electrodes are only poorly in contact with the patient and may easily slip out of place if the patient moves.

The object of the invention is to make possible a simplified adaptation of the individual electrodes to the shape of the body, particularly of the head, of the patient, and thereby allow more rapid progress in studying multiple patients.

This object is achieved according to the invention by a device for applying electrode assemblies to the surface of the skin of an animal or human, having the features of the predicate of the independent claim 1.

In a device with a plurality of electrode assemblies which may be applied to the surface of the skin of an animal or human and with which voltages and currents from the skin surface may be tapped, which device has a retaining element which is a flexible, particularly extendable flat or film-like moulded piece, it is provided according to the invention that the electrode assemblies each have a main body as well as a plurality of pin electrodes which protrude in the same direction from the main body, and the electrode assemblies are attached to the retaining element, further that the main body of a respective electrode assembly is connected to the retaining element, the pin electrodes of all of the electrode assemblies protruding in the same direction. This thereby allows simple positioning of the electrodes as well as simple adaptation of the positions of the electrodes on the respective patient.

In order to improve the adaptation to special body parts, it may be provided that the retaining element is in the form of a cover or a sleeve.

It may further be provided that a pervasive recess is provided in the main body of at least one of the electrode assemblies and particularly of all the electrode assemblies, through which recess a gel may be applied to the skin surface, when the pin electrodes are applied against the skin surface, which gel reduces the contact resistance between the skin surface and the pin electrodes.

It is thereby possible to achieve improved contact of the pin electrodes with the skin surface of the patient, thereby minimising the influence of movements of the patient during the measurement. Moreover there is the advantage that if the contact is sufficiently good it is possible to omit the use of a gel, thereby avoiding soiling of the patient with the gel. If it is possible to do without the use of a gel because of sufficient contact, a time-consuming application of gel is not required.

In order to facilitate the application of gel to the respective skin locations during measurement, it may be provided that the retaining element has recesses, the respective position of which is adapted to the position of each of the respective recesses in the main body, so that a gel may be applied to the skin surface through the recesses in the retaining element and through the recess in the main body.

In order to achieve particularly good application to the body of the patient, particularly in measurements of longer duration, it may be provided that the main body is flat or plate-shaped with two opposite surface regions, wherein the recess is a pervasive recess, and the boundary of the recess connects the two surface regions with each other.

For advantageous application of a gel to the pin electrodes and for reducing the contact resistance between the pin electrodes and the skin surface, it may be provided that the pin electrodes are fixed to the boundary of the recess on the main body.

For optimum distribution of the applied gel, it may be provided that the recess is circular.

Further, in order to improve the application stability of the electrode assembly to the skin of the patient, it may be provided that any two adjacent pin electrodes are separated by the same distance.

In order to achieve improved contacting of the pin electrodes and to reduce transmission errors, it may be provided that the pin electrodes are arranged on a common electrode ring, wherein the electrode ring is preferably comprised of the same material as the pin electrodes.

For advantageous penetration of the hair on the surface of the skin, and to achieve an advantageous application stability of the electrode assembly on the skin of the patient, it may be provided that the number, arrangement, and height or length of the pin electrodes are such that the pin electrodes may penetrate through hair on the skin surface and may provide a stable application; and/or that the height of the pin electrodes is between 1 mm and 30 mm.

For advantageous distribution of the gel on the skin surface, it may be provided that the area occupied by the surface of the main body of an electrode assembly which is excised to form the recess is from 0.785 to 700 $mm^2$, and/or the radius of the recess is between 1 mm and 30 mm.

In order to improve the contact between the skin surface and the pin electrodes, and to improve the mechanical application stability, it may be provided that the diameter of the pin electrodes is selected such that the pin electrode may penetrate through the hair on the skin surface but does however not hurt the skin surface at a contact pressure allowing electrical contact; and/or that the diameter of the pin electrodes is between 0.5 and 5 mm.

In order to improve the contact between the skin surface and the pin electrodes, and to avoid injury to the patient, it may be provided that the ends of the pin electrodes which are distal from the main body are hemispherical.

For durable electrical contacting and reduction of the contact resistance and contact voltage, it may be provided that the pin electrodes are highly conductive, and in particular are comprised of gold, TiN, $IrO_2$, or of an alloy comprised of gold and/or TiN, $IrO_2$.

In order to avoid electrical disturbances, e.g. due to electromagnetic interference, it may be provided that an amplifier assembly is provided and the pin electrodes are connected to the amplifier assembly. In this way, operation is possible even in the case of high skin resistance.

When the amplifier assembly is arranged on the main body, this enables simplified contacting of the electrodes.

Optimal amplification with minimum noise is possible when the maximum distance of the amplifier assembly to the closest pin electrode is less than 20 mm.

To facilitate easy exchangeability of electrodes as well as to reduce the number of amplifier assemblys, it may be provided that the amplifier assembly is arranged on a separate further main body which is electrically and mechanically removable and connectable to the main body, in particular through catch connections.

In order to guarantee a simple structure of the device according to the invention and rapid replacement of defective electrodes and replacement of amplifiers on further main bodies, it may be provided that the retaining element has a plurality of recesses, and the catch connections extend through the recesses of the retaining element.

BRIEF DESCRIPTION OF THE DRAWINGS

The invention will be described with reference to a number of examples, with reference to the appended drawings, without limiting the general inventive concept.

FIGS. 1a and 1b are perspective views of an electrode assembly of the present invention.

FIG. 1c is a cross sectional view of the electrode assembly of FIG. 1a.

FIG. 2b is a cross-section of the arrangement shown in FIG. 2a.

FIGS. 1a and 1b show two illustrations of an electrode assembly from different viewpoints. FIG. 1c shows the electrode assembly in cross-section. FIG. 2a illustrates a side view of a separately formed amplifier circuit on a further main body which is contacted with the electrode assembly illustrated in FIGS. 1a to 1c. FIG. 2b shows a cross-section of the arrangement shown in FIG. 2a. FIG. 3a illustrates a cover with an electrode assembly and interior. FIG. 3b illustrates the cover shown in FIG. 3a from the exterior. FIG. 4 illustrates a portion of a device for application against the skin surface, applied against a patient, in cross-section.

FIG. 5 illustrates an alternative electrode assembly according to the invention. FIG. 8 illustrates a separate amplifier circuit formed on a circuit board, which is contacted with an electrode assembly. FIG. 7 illustrates a cover with a plurality of electrode assemblies. In FIG. 8, part of a device for application against the skin surface, applied to a patient, is shown in cross-section.

DETAILED DESCRIPTION OF THE ILLUSTRATIVE EMBODIMENT

In FIGS. 1a to 1c, an embodiment of an electrode assembly 10 is illustrated. This comprises a main body 1 in the form of a circuit board. The main body 1 is essentially flat and has a thickness of 1.2 mm. The two surface areas 11 and 12 opposite to each other of the main body 1 are flat and parallel with each other. The main body 1 is circular.

Figure 4:
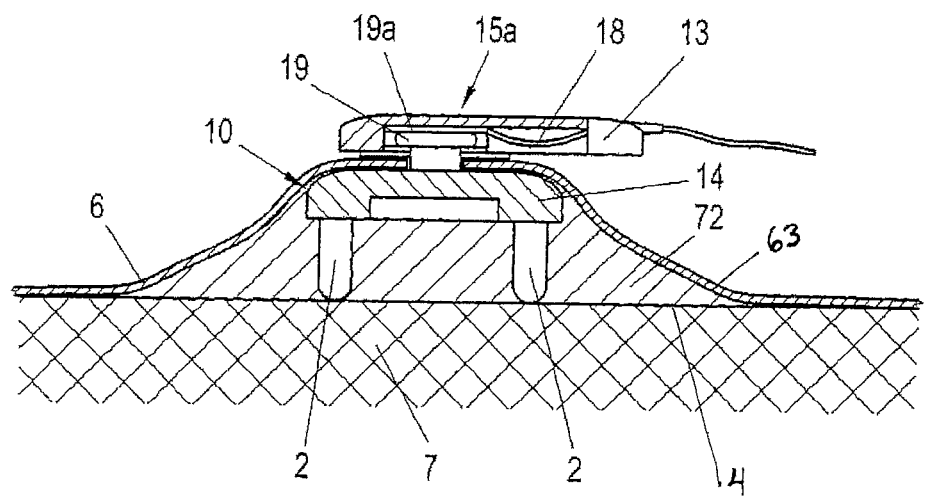
FIG. 4 is a cross-sectional view of a portion of a device of the present application against the skin surface of a patient.
Figure 8:
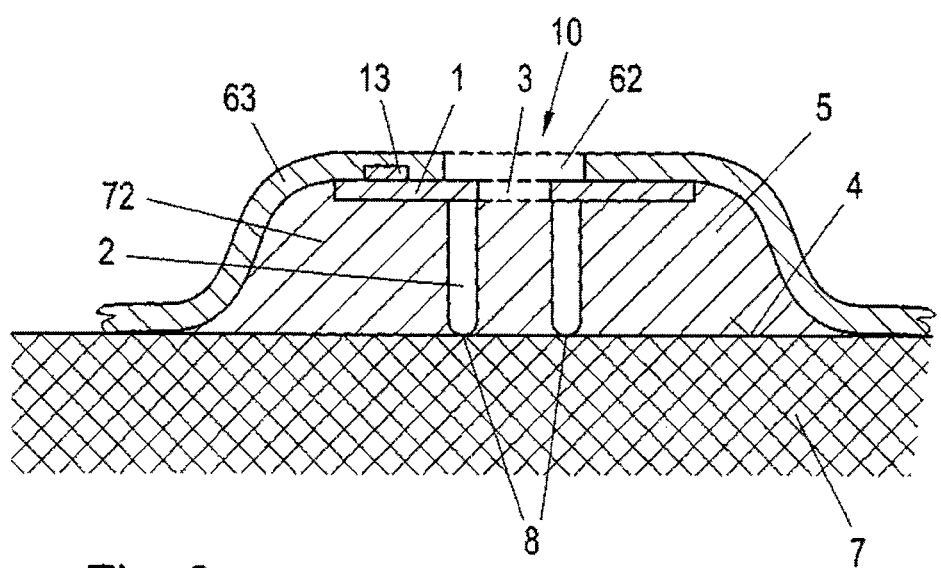
FIG. 8, is a cross-sectional view of a device of the present application against the skin surface of a patient.

In the region of the boundary of the circular main body 1, eight pin electrodes 2 are arranged which protrude from one of the surface regions 11. The number of such electrodes 2 is advantageously more than 3, to facilitate a mechanically stable application to the skin surface 4 of the patient 7 (FIGS. 4, 8). On the other hand, the number of electrodes 2 is selected such that sufficient distance is provided between the electrodes 2 to receive hairs, so that individual hairs of the patient 7 do not become caught between the electrodes 2 and the skin surface 4. The distance between two adjacent electrodes 2 is approximately twice the diameter of an electrode 2.

In the present embodiment, the pin electrodes 2 have a length of 7 mm and a diameter of 2.5 mm. The distal ends of the electrodes 2 have a hemispherical shape.

In the present embodiment, the pin electrodes 2 are comprised of pure gold, with a minimum of impurities.

Alternatively, however, other alloys may however be used; wherein, advantageously, the pin electrodes 2 have low electrical resistance. It is further advantageous if the pin electrodes 2 have high mechanical stability, particularly flexural strength and breaking strength, e.g. as is typically the case with alloys of TiN or $IrO_2$.

The main body 1 has an electrically highly conductive electrode ring 14 in its boundary region and in its area facing away from the pin electrodes 2, which ring is comprised of a gold alloy and is soldered to the pin electrodes 2. In the present embodiment, the electrode ring 14 forms a part of the main body 1 and has the form of a hollow cylindrical layer with a layer thickness of 1.2 mm, an inner radius of 11 mm, and an outer radius of 17 mm. The part 14a arranged in the interior of the main body 1 and surrounded by the electrode ring 14 is not conductive.

Alternatively, the entire main body 1 may be comprised of highly conductive material, particularly electrode material.

Alternatively, the pin electrodes 2 may be welded or otherwise electrically conductively and mechanically connected to the electrode ring 14.

Figure 2A:
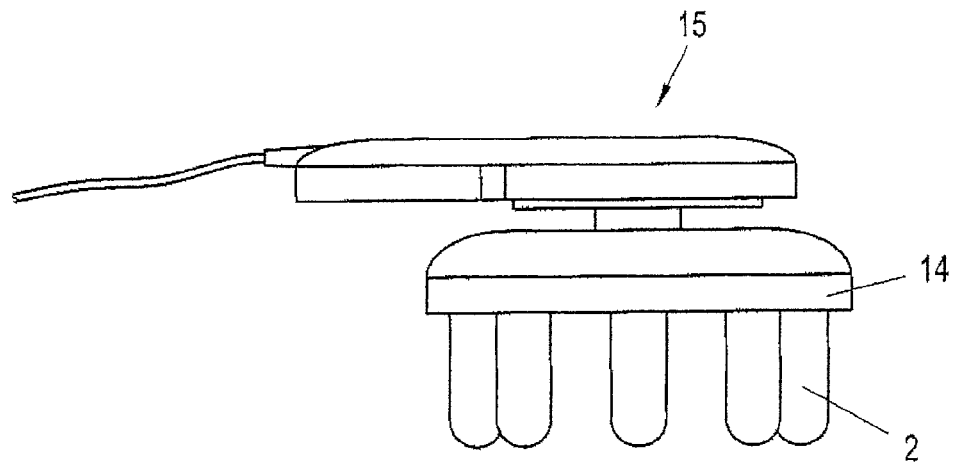
FIG. 2a is a side elevational view of a separately formed amplifier circuit on a further main body which is contacted with the electrode assembly illustrated in FIGS. 1a to 1c.
Figure 2B:
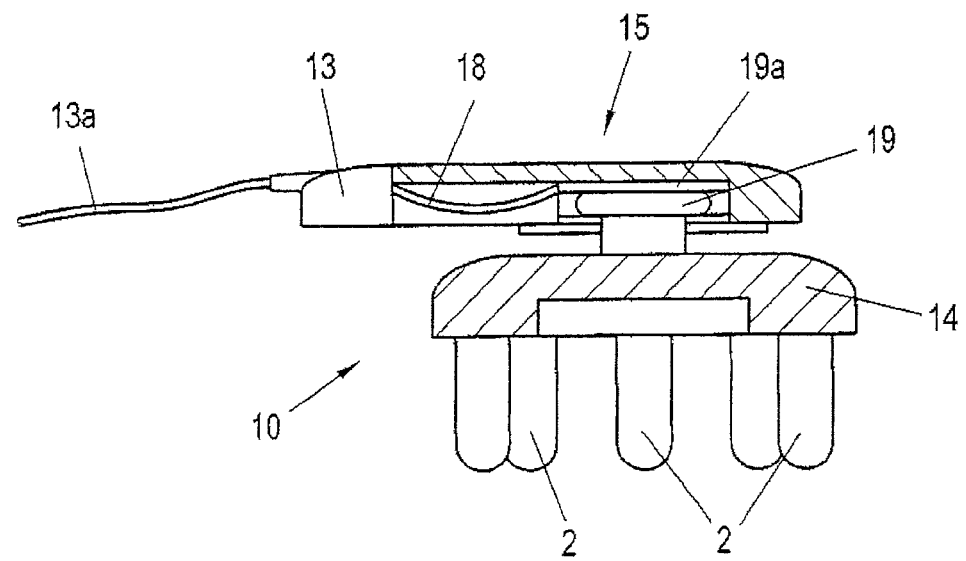

On the surface region 12 opposite to the surface region 11 from which the pin electrodes protrude, a connecting piece 19 is provided which is conductively connected to the electrode ring and thus with the individual pin electrodes 2. In the present case the connecting piece 19 is in the form of a catch piece which may be removably connected to a further connecting piece 19a (FIGS. 2a, 2b). The connecting piece 19 is also comprised of a material with good conductivity, in order to advantageously pass on the signals determined by the pin electrodes 2.

In FIGS. 2a and 2b the electrode assembly 10 illustrated in FIGS. 1a to 1c is electrically and mechanically connected via the connecting piece 19 to a further main body 15 which has a further connecting piece 19a which is electrically and mechanically connectable with the connecting piece of the electrode assembly.

In this way, a two-piece electrode assembly is illustrated having the illustrated main body 1 as well as the structure of the pin electrodes 2 corresponding to the embodiment illustrated in FIGS. 1a to 1c. An amplifier assembly 13 is arranged on the further main body 15. The main body 1 and the further main body 15 are electrically conductively interconnected by the respective connecting pieces 19 and 19a, with the further main body having a connecting line 18 between the further connecting piece 19a and the amplifier 13. The catch connection between the main body 1 and the further main body 15 is releasable and restorable without suffering any mechanical damage. The output signal of the amplifier 13 is transmitted via a cable 13a to a data processing unit.

Figure 3A:
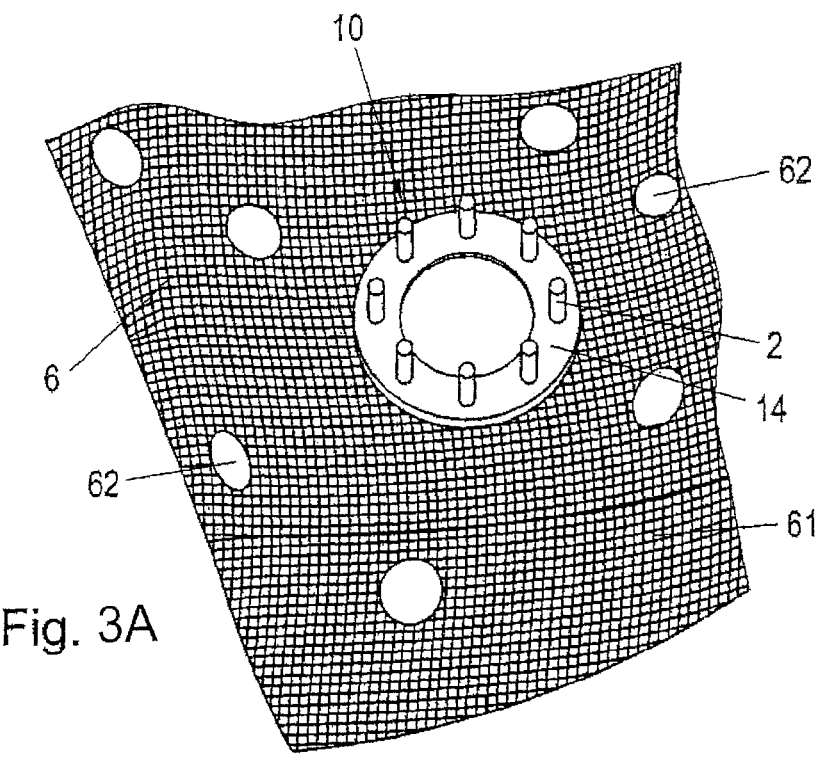
FIG. 3a is an elevational view of a cover with an electrode assembly and interior.
Figure 3B:
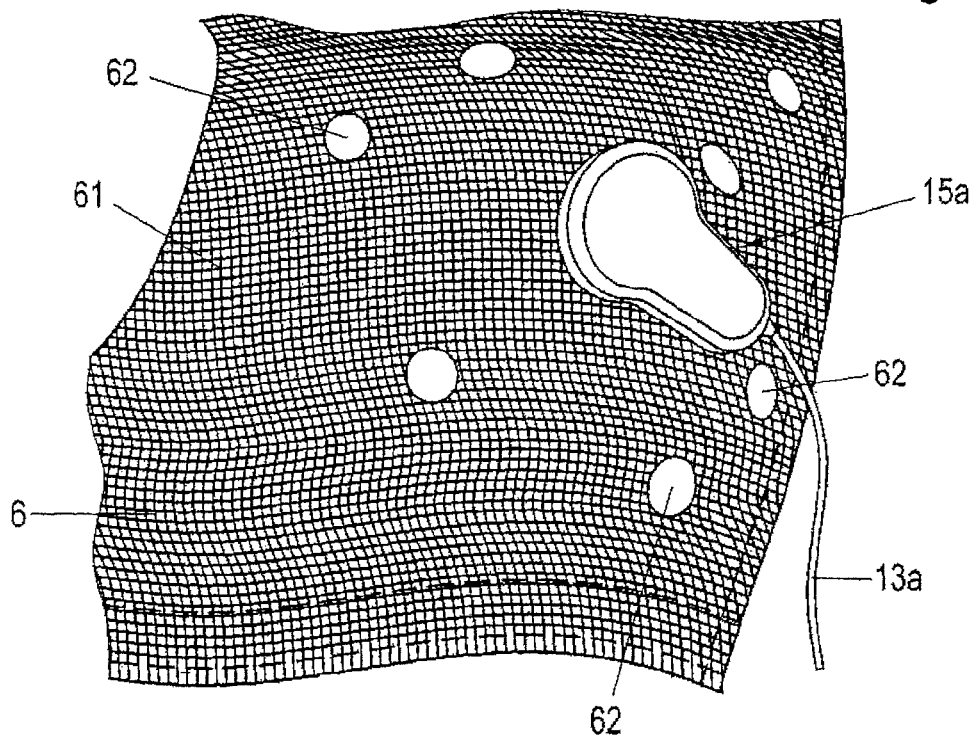
FIG. 3b is an elevational view of the cover shown in FIG. 3a from the exterior.

In FIGS. 3a and 3b a retaining element 6 in the form of a cover 61 is shown, from the inside and from the outside, with only one electrode assembly 10 and one further main body 15 being shown. The cover 61 is designed for application to the surface of the skin 4 on the head of a patient 7. The electrode assemblies 10 essentially correspond to the electrode assemblies 10 illustrated in FIGS. 2a and 2b. The main body of the electrode assemblies 10 lies against the inner side of the cover 61, with the further surface region 12 being in physical contact with the inner surface of the cover 61. The pin electrodes 2 extend into the interior of the cover 61. The cover 61 has recesses 62 in the regions of the catch connections 16 of the electrode assemblies 10, which recesses allow direct contacting with the further main body 15 (FIG. 4), so that the skin surface of the patient is directly electrically contactable through the cover 61.

The further main body 15 is on the outer side of the cover 61, wherein the side toward which the further connecting piece 19a is directed, is directed toward the cover 61, and is in electrical and mechanical contact with the connecting piece 19 which passes through the recess 62 in the cover.

In FIG. 4, the embodiment of the invention illustrated in FIGS. 3a and 3b is shown in cross section. The cover 62 has, as shown in FIGS. 3a and 3b, a plurality of electrode assemblies 10 arranged on its inner surface. The recesses 62 in the sleeve 63 are penetrated by the connecting piece 19 and 19a of the main body of the electrode assembly 10 and of the further main body.

An intermediate region filled with hairs between the skin surface 4 and the main body 1 is shown hatched, designated subsequently by "hair region 72". The main body 1 and the skin surface 4 of the patient 7 are held apart by the hair as well as by the pin electrodes 2.

Figure 5:
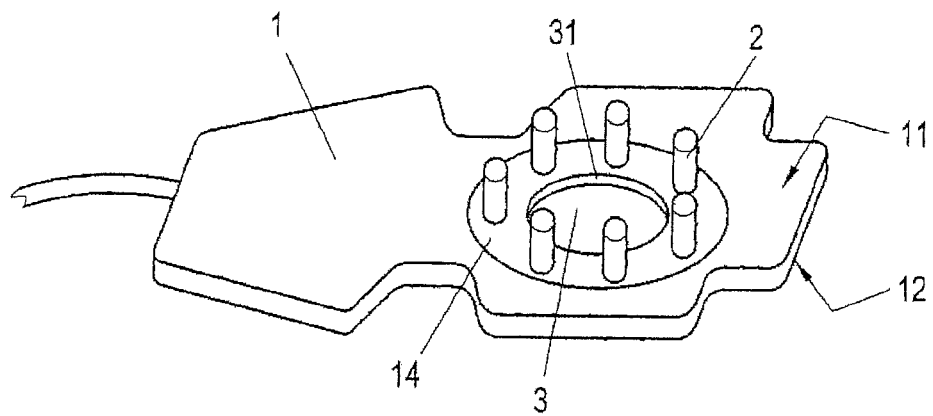
FIG. 5 is an elevational view of an alternative electrode assembly according to the invention.

FIG. 5 illustrates an alternative embodiment of an electrode assembly 10. This is comprised of a main body 1 in the form of a circuit board. The main body 1 is essentially flat, with thickness of 1.2 mm. The two surface regions 11 and 12 opposite to each other of the main body 1 are planar and parallel. A circular recess 3 is formed in the main body 1. In this preferred embodiment of the invention, the diameter of the recess 3 is 5 mm, and thus the radius is 2.5 mm. The recess 3, i.e. the excised surface of the main body 1 has an area of approximately 50 mm$^2$.

In the region of the boundary of the recess 3 there are seven pin electrodes 2 which protrude from one of the surface regions 11. Advantageously, the number of pin electrodes 2 is more than three, to facilitate a mechanically stable application to the skin surface 4 (FIG. 8) of the patient 7 (FIG. 8). On the other hand, the number of pin electrodes 2 is selected such that there is sufficient space between the pin electrodes 2 to receive hairs and to avoid a situation where individual hairs of the patient 7 become stuck between the pin electrodes 2 and the skin surface 4. The distance between adjacent pin electrodes 2 is approximately the diameter of a pin electrode 2.

In the present embodiment, the pin electrodes 2 have length 7 mm and diameter 2.5 mm. The ends of the pin electrodes 2 which are distal from the main body 1 have a hemispherical shape.

In the present embodiment, the pin electrodes are comprised of pure gold with a minimum of impurities.

Alternatively, however, other alloys may be used, wherein advantageously the pin electrodes 2 may have low electrical resistance. It is further advantageous if the pin electrodes 2 have high mechanical stability, particularly flexural strength and breaking strength, e.g. as is typically the case with alloys of TiN.

The main body 1 has in the region of the recess 3 an electrically highly conductive electrode ring 14 comprised of a gold alloy, to which the pin electrodes 2 are soldered. The electrode ring 14 has a square cross section of 10 mm×10 mm. The radius of the recess in the interior of the electrode ring 14 is 5 mm, and the area of the recess is 50 mm$^2$. Alternatively, the pin electrodes may be connected to the electrode ring 14 by welding or by other electrically conducting and mechanical means. The electrode ring 14 passes through the entire main body 1, wherein the surface extending in the direction of the central recess of the electrode ring 14 forms a boundary of a cylinder barrel form 31 of the recess 3 extending perpendicularly to the surface regions 11 and 12. The electrode ring 14 is connected to an amplifier assembly 13 (FIG. 8) by a highly electrically conductive connecting line arranged on the further surface region 12 (not shown in FIG. 5). Advantageously, in this embodiment this electrical connecting line is comprised of the same electrode material as the pin electrodes 2.

The amplifier assembly 13 is close to the individual pin electrodes, and in the present embodiment, for the purpose of minimising electromagnetic disturbances, the device 13 is arranged 4 mm away from the nearest pin electrode 2.

Figure 6:
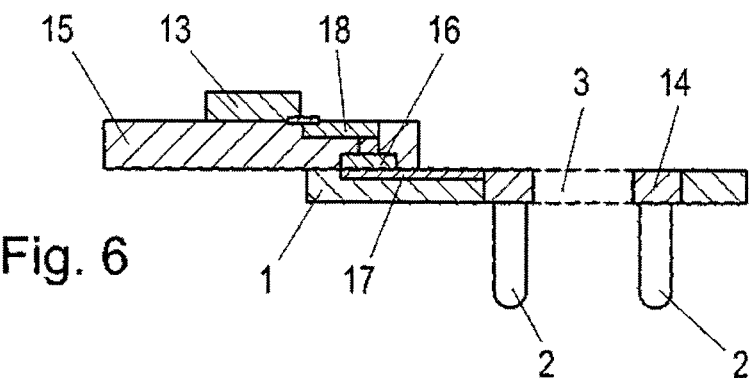
FIG. 6 is a cross sectional view of a separate amplifier circuit formed on a circuit board, which is contacted with an electrode assembly.

FIG. 6 illustrates an alternative two-piece electrode assembly 10, wherein the main body 1 as well as the arrangement of the pin electrodes 2 corresponds to the embodiment illustrated in FIG. 5. Unlike the embodiment illustrated in FIG. 5, the main body of the alternative illustrated in FIG. 6 has a further main body 15 on which the amplifier assembly 13 is arranged. The main body 1 and the further main body 15 are electrically conductively connected via respective connecting lines 17 and 18 on the main body 1 and on the further main body 15, and via a catch connection 16. The catch connection 16 enables releasable mechanical connection of the main body 1 and the further main body 15.

In the present embodiment, the electrical connecting lines 17 and 18 are in the form of connecting layers on the surfaces of the main bodies 1 and 15.

Figure 7:
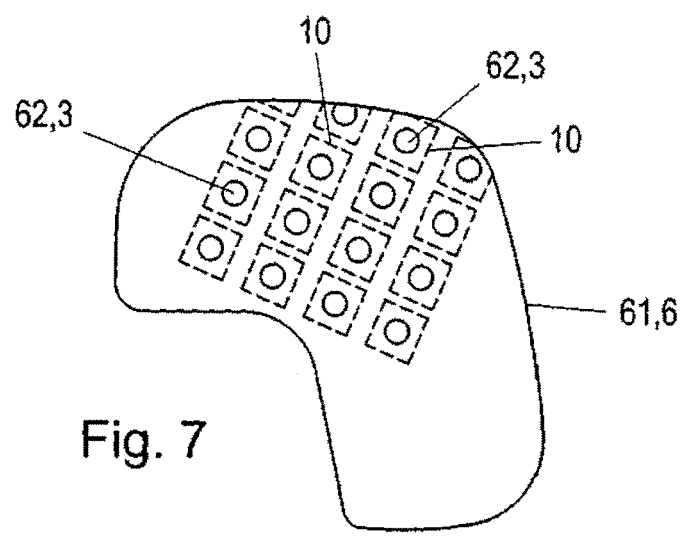
FIG. 7 is a plan view of a cover of the present invention with a plurality of electrode assemblies.

In FIG. 7 a retaining element 6 in the form of a cover 61, for being applied against the surface of the skin 4 on the head of a patient 7 is illustrated. The electrode assemblies 10 essentially correspond to those illustrated in FIG. 5. The main bodies 1 of the electrode assemblies 10 lie on the interior of the cover 61, wherein the additional surface area 12 is in mechanical contact with the inner surface area of the cover 61. The pin electrodes 2 extend into the interior of the cover 61. In the regions in which the recesses 3 of the electrode assemblies 10 are arranged, the cover 61 has recesses 62, so that a gel 5 (FIG. 8) may be applied directly from the exterior through the cover 61 and onto the skin of the patient 7. In the embodiment illustrated in FIG. 7, for example, this can readily occur because the recesses 62 of the cover 1 are aligned with the recesses 3 of the main body 1 of the respective electrode assembly 10.

Alternatively, however, it is also possible for the individual electrode assemblies 10 to be inserted into individual recesses 62 of the cover 61, with the cover 61 continuing in the region of its recess 62. In this case, the outer boundary of the electrode assembly 10 adjoins the inner boundary of one of the recesses 62 of the cover 61.

In FIG. 8 a part of a different embodiment of the invention is shown, in the form of a sleeve 63 which is in operation with the patient 7. The sleeve 63 has, similarly to the cover 61 shown in FIG. 7, a plurality of electrode assemblies 10 arranged on its inner surface. The recesses 62 in the sleeve 63 are aligned with the recesses 3 in the main body 1 of the electrode assembly 10, so that a gel 5 may be applied to the skin surface 4 of the patient 7. After the gel 5 is applied through the recess 3 it is arranged in the intermediate region filled with hair (indicated by hatched lines), hereinafter referred to as the hair region 72, between the skin surface 4 and the main body 1. The main body 1 and the skin surface 4 of the patient 7 are separated by the hair on the one hand and by the pin electrodes 2 on the other hand. The gel 5 diffuses into the hair region 72 and reaches the application points 8 of the pin electrodes 2 against the skin surface 4, used for substantially reducing the contact resistance.

In a case when there is already sufficient electrical contact and signals of sufficient quality for the respective study are available, the application of the gel 5 to the skin surface 4 in the hair region 72 may be omitted.

Alternatively to the gel 5, an aqueous foam or a wet sponge (neither illustrated) may be used, to be arranged in the recess 3 of the main body 1 and between the pin electrodes 2.

In order to prevent moisture or water from penetrating into the electrode assembly 10, the electrically active components of the electrode assembly 10 such as, e.g., the amplifier assembly 13, may have a waterproof design. The output signal of the amplifier 13 is transmitted by a cable (not shown in FIGS. 5 to 8) to a data processing unit.

Alternatively, it may be provided that the pin electrodes 2 are not comprised entirely of gold and/or TiN and/or IrO$_2$ or an alloy of gold and/or TiN and/or IrO$_2$, but rather of a supporting body, e.g. comprised of metal, which is only coated with one of the indicated highly conductive alloys.

The invention claimed is:

1. An apparatus with a plurality of electrode assemblies (10) which can be applied to the surface of the skin (4) of an animal or a human being, by which electrode assemblies voltages and currents can be picked up from the skin surface (4), which apparatus further has a flexible, extendable, retaining element (6) which is formed with a flat or film-like moulded piece, wherein the electrode assemblies (10) each have a main body (1) and a plurality of pin electrodes (2) which project in the same direction from the main body (1), the electrode assemblies (10) are attached to the retaining element (6), and the main body (1) of a given electrode assembly (10) is connected to the retaining element (6), and the pin electrodes (2) of all of the electrode assemblies (10) project in the same direction; characterized in that an amplifier device (13) is provided, the pin electrodes (2) are connected to the amplifier device (13), and the amplifier device (13) is disposed on a separate, additional main body (15), which may be electrically and mechanically connected to the respective main body (1) in a releasable manner.

2. The apparatus according to claim 1, characterized in that the retaining element (6) is embodied as a cover (61), or as a sleeve.

3. The apparatus according to claim 1, characterized in that a through-going recess (3) is provided in the main body (1) of the electrode assemblies (10), through which recess a gel (5) can be applied to the skin surface (4), when the pin electrodes (2) are applied against the skin surface (4), which gel reduces the contact resistance between the skin surface (4) and the pin electrodes (2).

4. The apparatus according to claim 3, characterized in that the retaining element (6) has recesses (62) the positions of which are coordinated with the positions of recesses (3) in main bodies (1), so that a gel (5) can be applied to the skin surface (4) through the recesses (62) in the retaining element (6) and through the recess (3) in the given main body (1).

5. The apparatus according to claim 3, characterized in that the main bodies (1) of the electrode assemblies (10) are flat or plate-shaped with two opposite surface regions (11, 12), wherewith the recesses (3) in the main bodies (1) have edges (31) that connect the two surface regions (11, 12) of each of the main bodies (1) with each other.

6. The apparatus according to claim 3, characterized in that the main bodies (1) of the electrode assemblies (10) are flat or plate-shaped with two opposite surface regions (11, 12), wherewith the recesses (3) in the main bodies (1) have a border and the pin electrodes (2) are affixed to the border of the recess (3) on the main bodies (1).

7. The apparatus according to claim 3, characterized in that the recess (3) in the electrode assembly (10) is circular.

8. The apparatus according to claim 3, characterized in that in each instance, any two neighbouring pin electrodes (2) of an electrode assembly (10) are separated by the same distance.

9. The apparatus according to claim 1, characterized in that the pin electrodes (2) are disposed on a mutual electrode ring (14), and are connected to the same in an electrically conducting manner, wherein the electrode ring (14) is composed of the same material as the pin electrodes (2).

10. The apparatus according to claim 1, characterized in that the height of the pin electrodes (2) is between 1 mm and 30 mm.

11. The apparatus according to claim 1, characterized in that the area of the main body (1) excluded by a respective recess (3) of the electrode assembly (10) is 0.785 mm$^2$ to 700 mm$^2$, and/or the radius of the respective recess (3) is between 1 mm and 30 mm.

12. The apparatus according to claim 1, characterized in that the diameter of the pin electrodes (2) is between 0.5 mm and 5 mm.

13. The apparatus according to claim 1, characterized in that the end of the pin electrodes (2) which is distal from the main body (1) is hemispherical.

14. The apparatus according to claim 1, characterized in that the pin electrodes (2) are highly conductive, and are comprised of gold, TiN, or an alloy containing gold and/or TiN and/or IrO2.

15. The apparatus according to claim 1, characterized in that the amplifier device (13) is provided on the main body (15) of the respective electrode assembly (10), at a distance of less than 20 mm from the closest pin electrode (2).

16. The apparatus according to claim 1, characterized in that the amplifier device (13) is disposed on the additional main body (15) which is electrically and mechanically connected to the respective main body (1) in a releasable manner via catch connections (16, 19, 19a).

17. The apparatus according to claim 16, characterized in that the retaining element (6) has a plurality of recesses (62), and the catch connections (19, 19a) extend through the recesses (62) of the retaining element (6).

* * * * *